(12) United States Patent
Weaver

(10) Patent No.: US 6,206,854 B1
(45) Date of Patent: Mar. 27, 2001

(54) CATHETER GARMENT

(76) Inventor: Kathleen M. Weaver, P.O. Box 1, Bovard, PA (US) 15619

( * ) Notice: Subject to any disclaimer, the term of this patent is extended or adjusted under 35 U.S.C. 154(b) by 0 days.

(21) Appl. No.: 09/566,516

(22) Filed: May 8, 2000

(51) Int. Cl.$^7$ .................................................. A61M 25/00
(52) U.S. Cl. ................... 604/174; 604/179; 128/DIG. 26
(58) Field of Search ..................... 604/174, 179, 604/345, 180; 128/DIG. 26

(56) References Cited

U.S. PATENT DOCUMENTS

| | | | |
|---|---|---|---|
| 4,578,062 | 3/1986 | Schneider | 604/174 |
| 4,582,508 | 4/1986 | Pavelka | 604/179 |
| 4,666,432 | 5/1987 | McNeish et al. | 604/174 |
| 5,403,285 | 4/1995 | Roberts | 604/179 |

Primary Examiner—John D. Yasko
(74) Attorney, Agent, or Firm—Craig G. Cochenour; Suzanne Kikel

(57) ABSTRACT

A catheter garment for receiving and retaining an indwelling catheter near the exit site on the body. The garment comprises a flexible band member with a middle portion, upper and lower portions defining an inner surface and an outer surface, and end portions with adjustable fastening means e.g. hook and loop means. An elongated pouch for receiving and retaining the external tubing portion is affixed to the inner surface of the garment and places the external tubing portion in close proximity to the patient's body when the garment is being worn. The elongated pouch is made of a rectangular piece of material that is folded over and its longitudinal free edges are sewn together. The pouch is then sewn along its sewn longitudinal edges onto the inner surface of the flexible band member. The elongated pouch has opened ends along opposite sides of the pouch. One opened end is diagonally formed i.e. slanted to easily receive the capped end and the external tubing portion for support of the external tubing portion along its length within the pouch during use or non-use of the indwelling catheter.

8 Claims, 2 Drawing Sheets

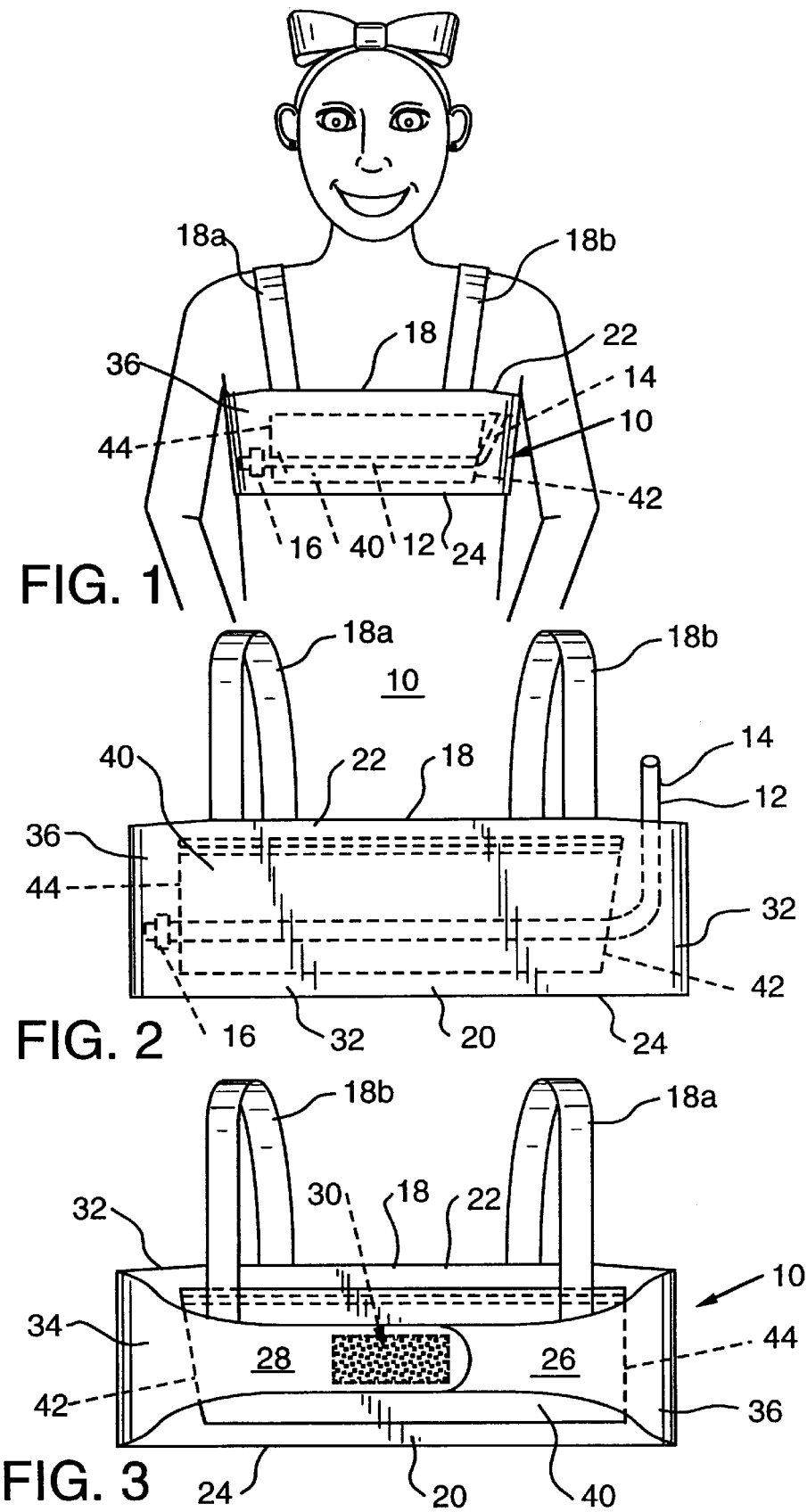

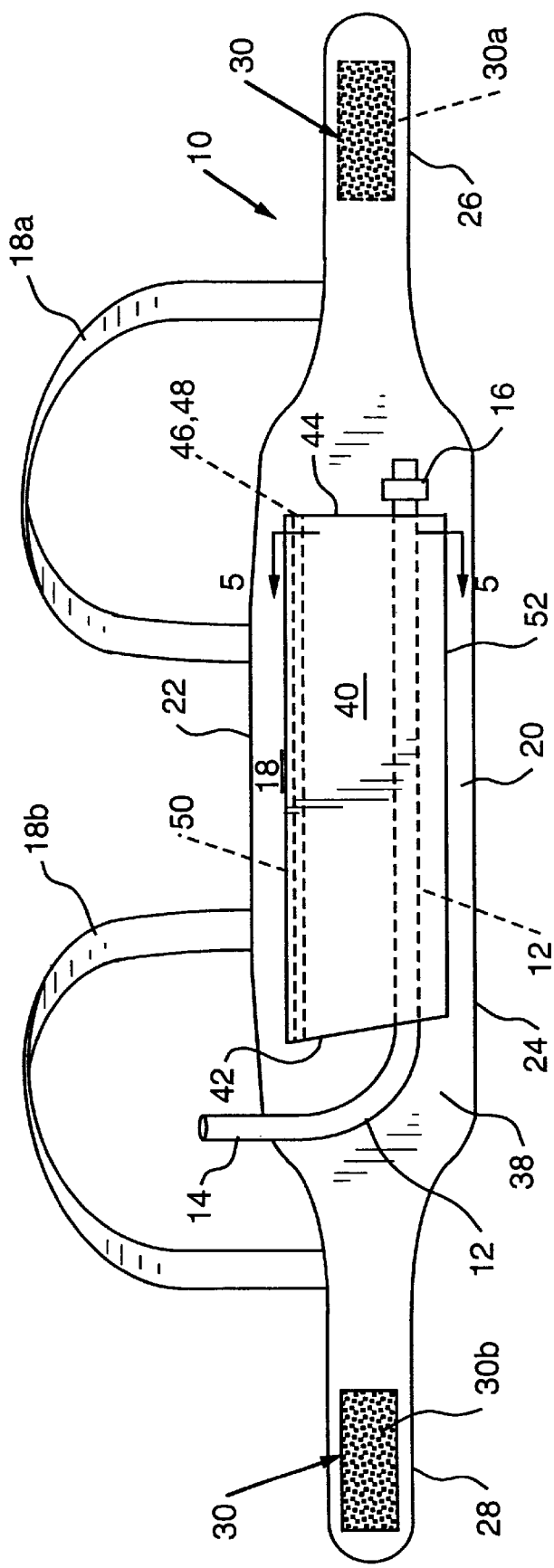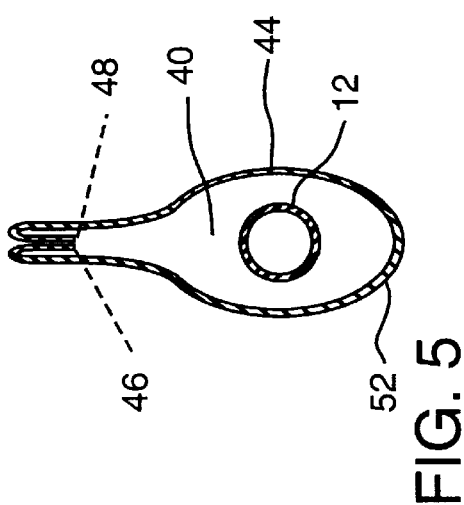
FIG. 4
FIG. 5

CATHETER GARMENT

1. FIELD OF THE INVENTION

The invention relates generally to a catheter garment for receiving and retaining indwelling catheters e.g. Hickman Broviac catheter device comprising one or more catheter tubes or similar devices to a patient's body.

2. BACKGROUND OF THE INVENTION

A Hickman Broviac indwelling catheter is generally flexible and is comprised of a small permanent rubber internal tubing portion that is surgically implanted into the right atrium of the heart; an external tubing extending from the exit site where the internal tubing portion extends from the patient's body; and an enlarged capped portion attached to the end of the external tubing portion.

Catheter tubes are used by the medical profession to provide easy access to a patient's circulatory system. Such a catheter is generally used for drawing blood, administering chemotherapy medications, and/or for giving blood products or other substances to the patient. A cancer patient who requires frequent blood tests or chemotherapy will have such a surgically implanted catheter. Even though a catheter such as the Hickman Broviac catheter requires daily care since it must be irrigated or flushed each day with a solution, it offers advantages to the patient. The alternative would be to endure the frequent administration of needles resulting in several needle punctures on the body. Such an implanted catheter also lessens the fears, anxiety and/or risks of skin infections generally associated with frequent needle use.

In the past, the externally extending catheter tubing portion of the implanted catheter extending from the exit site of the body with its capped free end were taped to the body to prevent displacement and/or dislodgment of the catheter. Each time the capped free end of the catheter was to be used, it was first necessary to remove the tape that secured the externally extending tubing portion to the body. Since the tube has to be flushed out at least once a day to prevent clogging, this meant that the tape had to be removed at least once a day. This frequent removal of the tape from the body generally resulted in sores and/or irritation to the body and thus, discomfort to the patient. Therefore, the tape-retention method for securing the catheter tube to the body was found to be highly undesirable and unsuitable. In addition to the sores and/or skin irritations, the tape did not afford the desired freedom of movement in that the patient constantly feared dislodgment of the catheter from its exit site on the body. Additionally, instead of being aesthetic the tape tended to be unsightly thereby creating mental distress especially to the more sensitive patients e.g. children.

When multiple catheter tubes were utilized, the mental distress in using the tape-retention method became even more pronounced, along with an increase in the difficulty and the pain associated with the tape removing and reapplying process.

Garments for holding and/or storing catheters or similar devices in various positions on or to the patient's body have evolved. These garments have lessened or eliminated many of the disadvantages inherent with the tape-retention method for the catheter tubes. Some of these garments or devices are described in the prior art.

In U.S. Pat. No. 4,578,062, Wilma F. Pavelka discloses a garment generally comprised of three elements including a triangularly shaped pocket for holding, storing, supporting, and receiving an indwelling catheter e.g. a Hickman Broviac device. A first strap-like element is attached to the triangularly shaped-pocket. This first strap-like element wraps the device around the patient's waist. A second strap-like element is connected to the triangularly-shaped pocket and to the first strap-like element to provide vertical support to the pocket and extends around the shoulder of the patient to position the garment against the upper torso of the patient. The inner surface of the pocket contains an opening through which the catheter is inserted for storage therein when the catheter is not in use and while the internal tubing portion is implanted into the body.

In U.S. Pat. No. 4,578,062, Paul E. Schneider discloses a catheter holder in the shape of a cut-off tank top body garment which is fitted securely around the patient's chest by an elastic band around the base of the garment. The holder is structured so as to provide a pouch on the inside of the tank top body garment and against the patient's chest. At the top of the pouch, a lip is formed by folding the fabric around another elastic band which maintains the shape of the pouch, which in turn supports the catheter tube when the tube is not in use but which tube is still implanted into the patient's body.

In U.S. Pat. No. 4,666,431, Kenneth McNeish etal discloses a halter and bra-type garment for retaining a catheter particularly of the Hickman Broviac type having one or two tubes. The catheter-retaining garment comprises a pocket on its outer surface. A slot or opening in the inner surface of the garment allows for receipt of the tubing which generally is stored in the pocket in coiled form while the internal tubing portion is anchored in the patient's body for its connection to the patient's heart.

In U.S. Pat. No. 5,403,285, Sandra L. Roberts discloses an apparatus for securing a catheter tube to a patient's body. An elongated, flexible, elastic member is adapted to extend completely around the chest of a person and over the flexible tube at the location where the tube exits the body. Hook and loop closure members are provided on the flexible member for holding the tube in a coiled position adjacent to the flexible member which tube extends through an opening in the flexible member adjacent to the chest of the patient. A flap is provided on the outer surface of the flexible member for selectively covering up the coiled tube when the tube is not in use. This flap allows easy access to the tube for adding medications, drawing blood, and/or for changing the apparatus so that the apparatus can be washed, cleaned, and re-used. The flexible band has hook and loop fasteners on the ends thereof so that the apparatus can be easily stretched and fastened around the patient's waist.

The prior art discussed herein above discloses a device or a garment having a pouch or pocket means for retaining an indwelling catheter to a patient's body. These devices and/or garments focus more on supporting the external tubing in coiled form when the catheter is not in use, and the pouch or pocket that is provided is generally of a dimension to only accommodate the external tubing when it is in coiled form. In most of these garment and/or devices the external tubing portion needs to be removed from the pocket or pouch in order to be used effectively. For some of these garments, the pocket is located conspicuously on the front of the garment for access to the catheter tube.

There is therefore a need in the medical profession for a garment and/or apparatus which not only allows for easy storage of a catheter when it is not in use, but which also substantially supports the catheter in an inconspicuous manner when in use, e.g. as medication and other substances are being administered into the blood stream of a patient or as blood is being withdrawn for testing.

SUMMARY OF THE INVENTION

The invention has met this need. The invention pertains to a catheter garment for receiving and retaining an indwelling catheter near the exit site on the patient's body when the garment is worn. The garment comprises a flexible band member with a first end portion and a second end portion, a middle portion, upper and lower portions that define an outer surface and an inner surface, and shoulder straps. The flexible band member extends completely around the body to create a frontal portion and a back portion where the first and second end portions overlap and which end portions have adjustable fastening means e.g. hook and loop fasteners for adjustably securing the flexible band member around the body. The shoulder straps are attached to the upper portion of the flexible band member at the front and back portions of the flexible band member. An elongated pouch is located along the inner surface of the flexible band member. The elongated pouch receives and supports at least the external tubing portion of the indwelling catheter along its length and positions the external tubing portion against the body. The external tubing portion is fully supported preferably in its extended position against the body when the indwelling catheter is either in use or in non-use. That is, the external tubing does not need to be in coiled form when the catheter is in its non-use mode. When the catheter is not in use, the capped end of the external tubing portion can be neatly tucked away into the elongated pouch or it can extend out of the elongated pouch and still be retained out of sight and inside the garment.

The elongated pouch is comprised of a piece of material preferably fabric, that is folded once over. The longitudinal free edges are then fixedly attached together, e.g. by stitches to form a first opened end and a second opened end. The first and second opened ends are located along the sides of the elongated pouch to provide access into the elongated pouch through the sides thereof. The elongated pouch at its longitudinal fixed edges is then fixedly secured e.g. by stitches to the inner surface of the middle portion of the flexible band member. This construction forms a freely swinging pouch that extends down and along the inner surface of the flexible band member. The elongated pouch is of a dimension so as to adequately receive and support the external tubing in its extended form. For placement of the external tubing portion into the elongated pouch, the capped end of the external tubing portion is first inserted into the first opened end of the elongated pouch. Preferably, this first opened end is formed on a diagonal i.e. slanted inward from the upper portion downwardly to the lower portion of the flexible band member for easy insertion, i.e. easy sliding of the capped end into the elongated pouch. After the capped end is inserted into the first opened end it is drawn completely into the pouch so that the external tubing portion is supported along its length in the elongated pouch along its length. The capped end can be placed near the second opened end of the pouch for storage within the pouch. Alternatively, the capped end can be allowed to hang freely out of the second opened end during storage of the elongated tubing portion within the garment or in readiness for use of the catheter while the external tubing portion remains supported along its length in the pouch.

The material for the components of the catheter-retaining garment of the invention preferably is a fabric of natural or synthetic fibers e.g. silk, flannel, wool, cotton, rayon, etc. or combinations thereof, and may contain a pattern or design e.g. ribbons, bows, cartoon characters, cowboy motif etc. as to create aesthetic appeal for the wearer.

It is therefore an objective of the present invention to provide a catheter-retaining garment which in an inconspicuous manner allows for easy storage of the external tubing portion and capped end of an indwelling catheter in either coiled form or extended form when it is in non-use, and allows for support of the external tubing of the catheter along its length when the catheter is in use.

A further objective of the present invention is to provide a catheter-retaining garment that protects the exposed end of the indwelling catheter by safely and inconspicuously storing it near the patient's body in a manner to allow the patient to move about freely with the internal tubing portion of the catheter in place within the body. Medical adhesive tape is eliminated, thereby avoiding the irritation and possible skin infections commonly associated with prolong use of adhesive tape.

Another objective of the present invention is to provide a garment for selectively supporting the external tubing portion and the capped end of an indwelling catheter in coiled form or uncoiled form and in close proximity to the exit site of the implanted catheter on the body and whereby the external tubing portion extending from the exit site can be continuously supported by the garment along its length regardless of whether the catheter is in use or in non-use. The external tubing portion is prevented from hanging down freely from the exit site on the body which condition may cause pain and/or discomfort to the patient.

A still further objective of the present invention is to provide a catheter supporting garment which is made of a comfortable material and which can be made in gaily colors or patterns, thereby lessening or alleviating some of the mental distress generally associated with the medical condition requiring catheter usage.

These and other objectives of the present invention will be better appreciated and understood by those skilled in the art from the following description of the drawings and the claims.

BRIEF DESCRIPTION OF THE DRAWINGS

FIG. 1 is a front view of the garment of the invention shown in operative connection to a patient's body.

FIG. 2 is an enlarged front view of the garment of the invention shown in assembled form and better illustrating an elongated pouch supporting the external tubing portion and a capped end of a catheter.

FIG. 3 is an enlarged rear view of the garment of the invention in assembled form without the external tubing portion and the capped end of the catheter.

FIG. 4 is a rear view of the garment of the invention where the first and second end portions of the garment are unattached and the elongated pouch is shown supporting in extended form the external tubing portion and capped end of a catheter.

FIG. 5 is a sectional view taken along lines 5—5 of FIG. 4 illustrating in exaggerated form a second opened end of the elongated pouch and the external tubing portion supported in the elongated pouch.

DETAILED DESCRIPTION OF THE INVENTION

FIG. 1 illustrates the catheter-retaining garment 10 of the invention being worn by a patient. An indwelling catheter has been surgically implanted into the patient's chest. The indwelling catheter has a flexible internal tubing portion (not shown) received within the body and a flexible external tubing portion 12 with a free end 14 extending from an exit site on the patient's body. Opposite to the free end 14 of the external tubing portion 12 is a capped end 16 which can be opened i.e. the capped is removed when infusing and withdrawing fluids from the body.

FIGS. 2 through 5 more clearly illustrate the catheter garment 10 embodying the invention. With particular reference to FIG. 4, the catheter-retaining garment 10 comprises a flexible band member 18 made of a flexible material, preferably a fabric made from natural or synthetic fibers, e.g. flannel, wool, rayon, cotton or silk. Flexible band member 18 has a middle portion 20, an upper portion 22, a lower portion 24, and a first end portion 26, and a second end portion 28. End portions 26,28 are provided with fastening means 30, e.g. hook and loop means as shown at 30a and 30b. When end portions 26,28 are secured together by fastening means 30, flexible band member 18 provides an enclosed continuous form that in turn provides a front portion 32 and a back portion 34 (best shown in FIG. 3). Shoulder straps 18a and 18b are fixedly secured e.g. by stitches to upper portion 22 at the front and back portions 32,34 of flexible band member 18.

Upper portion 22 and lower portion 24 define an outer surface 36 (FIGS. 1 and 2) and an inner surface 38 (FIG. 4).

Still referring to FIG. 4, inner surface 38 supports an elongated pouch 40. Pouch 40 receives and supports along its length the external tubing portion 12 of the indwelling catheter and positions the external tubing portion 12 along its length inside garment 10 in close proximity to the patient's chest when garment 10 is worn as best shown in FIG. 1. In FIG. 2, end portions 26, 28 are not shown for clarity, i.e. to more clearly illustrate the elongated pouch 40.

Still referring to FIG. 4, elongated pouch 40 has a first opened end 42 and a second opened end 44. First and second opened ends 42, 44 are located along the sides of elongated pouch 40 to provide access therein through the opposite sides of elongated pouch 40. First opened end 42 preferably is diagonally formed, i.e. slated inward from upper portion 22 downwardly toward lower portion 24 so that capped end 16 of external tubing portion 12 can be easily slid or inserted into elongated pouch 40 for support of external tubing portion 12 by garment 10.

FIG. 5 best illustrates second opened end 44 with external tubing portion 12 supported in elongated pouch 40. Elongated pouch 40 is generally comprised of a rectangular piece of material that is folded over once as shown best in FIG. 5. Its longitudinal free edges 46, 48 are then folded over and fixedly attached together, preferably by stitches. For clarity, these stitches are not shown in FIG. 5. Elongated pouch 40 is then fixedly secured (indicated at 50 in FIG. 4), preferably by stitches, along its longitudinal edges 46, 48 to inner surface 38 near upper portion 22 of flexible band member 18.

This construction for elongated pouch 40 and its cantilever attachment to inner surface 38 allow pouch 40 to swing freely down and across inner surface 38. In effect, elongated pouch 40 supports external tubing portion 12 in a sling-like manner. As best shown in FIG. 4, elongated pouch 40 substantially covers middle portion 20. The dimensions for elongated pouch 40 will vary according to the size of the garment 10, but in general are such that pouch 40 has sufficient area or capacity to adequately support external tubing portion 12 along its length. The structure and placement of pouch 40 easily places external tubing portion 12 inconspicuously across the body of the patient when garment 10 is worn. Even though elongated pouch 40 is disclosed as being fixedly secured to inner surface 38 only along its longitudinal edges 46 and 48, it can be appreciated that the lower folded portion 52 (FIGS. 4 and 5) of elongated pouch 40 can be fixed or sewn to inner surface 38.

In referring to FIG. 4 and in placement of external tubing portion 12 into elongated pouch 40, capped end 16 is first inserted into first opened end 42 and then drawn, i.e. pulled or pushed, completely into pouch 40 such that external tubing portion 12 is supported along its length along the length of the elongated pouch 40 and capped end 16 either is located in or extends out of second opened end 44.

Garment 10 with external tubing portion 12 supported therein may be worn either when the catheter is in use or when the catheter is in non-use. When the catheter is in use, i.e. the cap (not shown) on capped end 16 is removed and connected to an infusing or withdrawing fluid means (not shown), external tubing portion 12 may be supported in elongated pouch 40 in the same manner shown in FIGS. 1 and 4 which represent the catheter in its non-use. When the catheter is not in use capped end 16 can extend out of elongated pouch 40 or it can be neatly tucked into elongated pouch 40 at its second opened end 44. Alternatively, capped end 16 if extending excessively from second opened end 44 can be held in place inside garment 10 by lower portion 24 being tightly secured around the patient's body. When the catheter is in use capped end 16 is opened and attached to a fluid tube in a manner known to those in the medical profession.

Adjustment of flexible band member 18 around a patient's body e.g. chest can be accomplished by varying the amount of overlap of first and second end portions 26, 28. Even though not shown, straps 30a 30b can be structured to be adjustable through means well known to those in the garment industry, for example, through hook and loop means, snaps, slider means, etc.

Preferably, the components of garment 10 are made of the same material, which preferably is made of natural or synthetic fibers. This material may contain a pattern or design or may be solid colors.

Even though the invention illustrated and disclosed herein involves a catheter with one tube, it can be appreciated that the invention can be used effectively with any number of tubes in the elongated pouch in that the elongated pouch provides adequate support for the additional weight of the tubes.

While the present invention has been particularly set forth in terms of a specific embodiment thereof, it will be understood in view of the instant disclosure that numerous variations upon the invention are now enabled yet reside within the scope of the invention. Accordingly, the invention is to be broadly construed and limited only by the scope and spirit of the claims now appended hereto.

What is claimed is:

1. A catheter garment for retaining an indwelling catheter to the body, wherein the indwelling catheter has a flexible internal tubing portion received within the body and a flexible external tubing portion with a free end extending from the exit site on the body and a capped end for connection of catheter means to means for the administration of fluids and/or medication into the flexible external tubing portion and/or the withdrawal of blood therefrom, said garment comprising:

a flexible band member having a first end portion and a second end portion, a middle portion disposed between said first end portion and said second end portion, and an upper portion and a lower portion defining an outer surface and an inner surface;

said flexible band member adapted to extend completely around the body to create a frontal portion and a back portion and wherein said first end portion and said second end portion of said band member each has adjustable fastening means for adjustably securing said flexible band member around the body;

said flexible band member further having an elongated pouch extending substantially along said inner surface adjacent to the body for receiving and retaining the external tubing portion of the indwelling catheter substantially along its length so that the external tubing portion is fully supported and in close proximity to the body;

said elongated pouch having a first opened end and a second opened end, each said first opened end and said second opened end extending between said upper portion and said lower portion of said flexible band member, whereby when said external tubing portion is received and retained in said elongated pouch said external tubing portion extends through at least said first opened end of said elongated pouch.

2. A catheter garment of claim 1 wherein said elongated pouch is comprised of a piece of material folded over and the longitudinal free ends are fixedly attached together and to said inner surface of said flexible band member to form said first opened end and said second opened end of said elongated pouch.

3. A catheter garment of claim 1 wherein said first opened end and said second opened end are located along the opposite sides of said elongated pouch for access into said elongated pouch through said sides thereof.

4. A catheter garment of claim 1 wherein said first opened end of said elongated pouch is diagonally formed and extends inwardly from said upper portion downwardly toward said lower portion of said flexible band member.

5. A catheter garment of claim 1 wherein said adjustable fastening means of said first end portion and said second end portion comprises hook and loop means.

6. A catheter garment of claim 1 further comprising shoulder strap means secured to said upper portion of said flexible band member at said frontal portion and at said back portion of said flexible band member.

7. A method for inserting a catheter tubing into the catheter garment of claim 1 comprising:

inserting the capped end of the external tubing portion into said first opened end of said elongated pouch; and drawing said capped end through said elongated so that the external tubing portion is substantially supported in and by said elongated pouch.

8. A method of claim 7 further comprising: extending the capped end out of said second opened end of said elongated pouch for the selective connection of said capped end and said external tubing portion to said means for the administration of fluids and/or medication into the external tubing portion and/or withdrawal of blood therefrom while said garment is worn by the patient.

* * * * *